United States Patent [19]

Meilland

[11] Patent Number: Plant 7,116

[45] Date of Patent: Jan. 23, 1990

[54] ROSE PLANT—MEINEBLE VARIETY

[75] Inventor: Alain A. Meilland, Antibes, France

[73] Assignee: The Conard-Pyle Company, West Grove, Pa.

[21] Appl. No.: 288,579

[22] Filed: Dec. 22, 1988

[51] Int. Cl.[4] ..... A01H 5/00

[52] U.S. Cl. ..... Plt./1

[58] Field of Search ..... Plt. 1

*Primary Examiner*—Robert E. Bagwill

*Attorney, Agent, or Firm*—Burns, Doane, Swecker & Mathis

[57] ABSTRACT

A new and distinct variety of shrub rose plant is provided which forms in abundance attractive stable long lasting single guardsman red blossoms having a white center. The variety exhibits a strong creeping growth habit, and very good resistance to disease. The petals of the blossoms drop off cleanly. The new variety is well adapted for growing as a landscape planting.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the Sea Foam variety (U.S. Plant Pat. No. 2,463). The male parent (i.e., the pollen parent) of the new variety was the result of the pollination of the Picasso variety (U.S. Plant Pat. No. 3351) by the MACeye variety (U.S. Plant Pat. No. 3985). The MACeye variety is sometimes known as the Eye Paint variety. The parentage of the new variety can be summarized as follows:

Sea Foam × (Picasso × Maceye).

The seeds resulting from the above pollination were sown and 32 plantlets were obtained which were physically and biologically different from each other. Selective study resulted in the identification of a single plant of the new variety.

It was found that the new variety of shrub rose plant of the present invention possesses the following combination of characteristics:

(a) forms attractive stable and long lasting single guardsman red blossoms having a white center,
(b) exhibits a strong creeping growth habit,
(c) exhibits very good resistance to diseases, and
(d) is particularly well suited for growing in the landscape.

The new variety well meets the needs of the horticultural industry. It can be grown to advantage as an attractive ornamentation in parks, gardens, public areas, and residential landscapes. It is particularly well suited for growing in the landscape.

The characteristics of the new variety have been found to be homogeneous and stable and are strictly transmissible by all forms of asexual propagation such as budding, grafting, and cuttage from one generation to another.

The new variety has been named the Meineble variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the new variety described herein were three years old and were being grown in the open air during September on their own roots at Cannet-des-Maures, Var, France.

DETAILED DESCRIPTION

Figures 1, 2, 3, 4, 5, 6, 7, 8, 9, 10, 11, 12, 13, 14, 15, 16, 17:
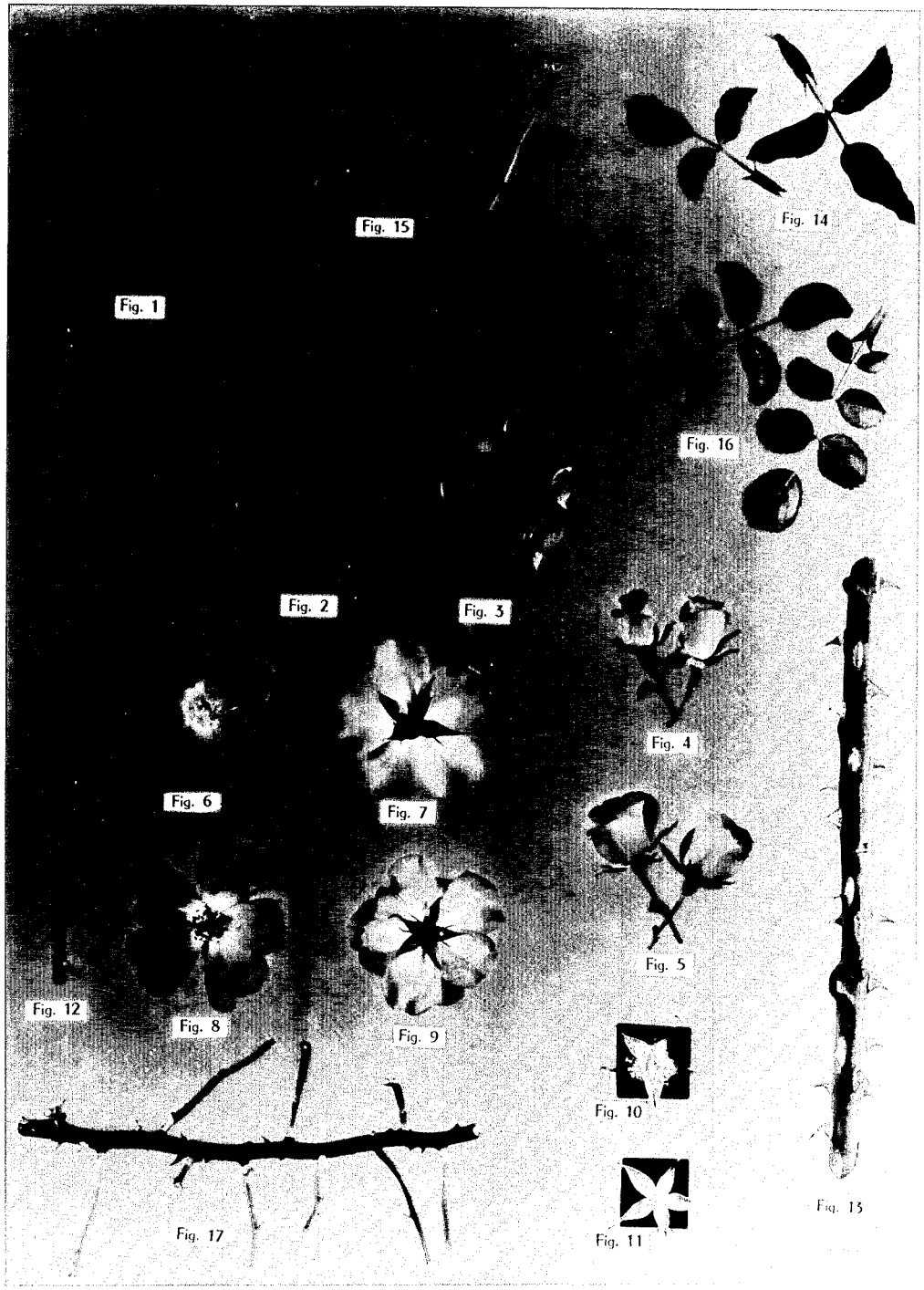
FIG. 1 illustrates a specimen of a young shoot.
FIG. 2 illustrates a specimen of seven floral buds before the opening of the sepals.
FIG. 3 illustrates a specimen of six floral buds at the opening of the sepals.
FIG. 4 illustrates specimens of two floral buds as the petals open.
FIG. 5 illustrates specimens of two flowers in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering shoot.
FIG. 13 illustrates a specimen of the adult wood of a main branch.
FIG. 14 illustrates specimens of leaves with three leaflets with the under surface being shown on the left and the upper surface being shown on the right.
FIG. 15 illustrates specimens of leaves with five leaflets with the upper surface being shown on the left and the under surface being shown on the right.
FIG. 16 illustrates specimens of leaves with seven leaflets with the upper surface being shown on the left and under surface being shown on the right.
FIG. 17 illustrates a specimen which shows the structure of the branches and stems.

The chart used in the identification of colors is that of The Royal Horticultural Society (R.H.S. Colour Chart). The description is based on three-year old specimens of the new variety during September while grown in the open air on their own roots at Cannet-des-Maures, Var, France.

Class: Shrub.

Plant:

*Height.*—Approximately 30 to 45 cm. on average.

*Habit.*—Creeping.

Branches:

Color.—Young stems: reddish brown. Adult wood: light green, Yellow-Green Group 146C.

*Thorns.*—Average.

Leaves:

*Stipules.*—Adnate, pectinate, wide and linear.

*Petioles.*—Upper surface: striped reddish-brown on young foliage, medium green on mature foliage with more or less glandular edges. Under surface: light green with a few prickles.

*Leaflets.*—Number: 3, 5, and 7. Shape: oval. Serration: single and regular. Texture: Leathery. Overall appearance: very dense foliage with a semi-dull aspect. Color (young foliage): upper surface: medium green, Yellow-Green Group 146B. under surface: light green, Yellow-Green Group 146C. Color (adult foliage): upper surface: dark green, Yellow-Green Group 137A. under surface: medium green, Yellow-Green Group 147A.

Inflorescence:

*Number of flowers.*—Approximately 1 to 15 blossoms per floral stem.

*Peduncle.*—Light green, straight, rigid, bears reddish glandular prickles, approximately 3.5 cm. in length on average.

*Sepals.*—Upper surface: tomentose and greenish. Under surface: light green, smooth edges, the outside sepals commonly have slightly appendiculated edges.

*Buds.*—Shape: conical. Length: approximately 1.5 cm. on average. Size: average. Color (when opening): upper surface: guardsman red, Red Group 45A with a white eye. under surface: tyrian purple, Red-Purple Group 57A.

*Flower.*—Form: cuplike, flat and single. Diameter: approximately 7 cm. on average. Color (when opening begins): upper surface: guardsman red, Red Group 45A with a white eye. under surface: tyrian purple, Red-Purple Group 57A. Color (when blooming): upper surface: guardsman red, Red Group 45A with a white eye. under surface: tyrian purple, Red-Purple Group 57A. Color (at end of blooming): upper surface: dark rose bengal, Red-Purple Group 57B with a white eye. under surface: rose bengal, Red-Purple Group 57C. Fragrance: none. Flower duration: very long. Petal form: rounded at the top with a more or less corrugated wedge-shaped base. Petal texture: consistent. Petal number: approximately 5 to 9 on average. Petal drop: good. Stamen number: approximately 87 to 93 on average. Anthers: normal, bright yellow. Filaments: free, yellowish and of irregular heights. Pistils: approximately 18 to 22 on average. Stigmas: greenish. Styles: free, greenish, of irregular heights. Receptacle: light green, smooth, and pear-shaped in longitudinal section.

Development:

*Vegetation.*—Very vigorous, very strong and abundant.

*Blossoming.*—Very abundant and continuous.

*Aptitude to bear fruits.*—Good.

*Resistance to frost.*—Very good.

*Resistance to diseases.*—Very good.

I claim:

1. A new and distinct variety of shrub rose plant characterized by the following combination of characteristics:

(a) forms attractive, stable and long lasting single guardsman red blossoms having a white center, (b) exhibits a strong creeping growth habit, (c) exhibits very good resistance to diseases, and (d) is particularly well suited for growing in the landscape;

substantially as herein shown and described.

* * * * *